United States Patent
Friese et al.

[11] Patent Number: 6,074,694
[45] Date of Patent: Jun. 13, 2000

[54] PROCESS OF APPLYING MATERIAL, IN PARTICULAR FOR THE PRODUCTION OF ELECTRODES FOR EXHAUST GAS SENSORS

[75] Inventors: Karl-Hermann Friese, Leonberg; Siegfried Nees, Neckarwestheim; Frank Stanglmeier, Moeglingen; Hans Baumann, Sternenfels, all of Germany

[73] Assignee: Robert Bosch GmbH, Stuttgart, Germany

[21] Appl. No.: 08/827,679

[22] Filed: Apr. 10, 1997

[30] Foreign Application Priority Data

Apr. 10, 1996 [DE] Germany ............... 196 14 147

[51] Int. Cl.[7] ............... B05D 1/02; B05D 3/12
[52] U.S. Cl. ............... 427/233; 427/123; 427/125; 427/126.5; 427/236; 427/421; 427/426; 427/427
[58] Field of Search ............... 427/123, 125, 427/126.5, 421, 426, 427, 233, 236

[56] References Cited

U.S. PATENT DOCUMENTS

| | | | |
|---|---|---|---|
| 3,007,810 | 11/1961 | Hobrock | 117/96 |
| 3,916,071 | 10/1975 | Kinnebrew et al. | 428/376 |
| 4,127,424 | 11/1978 | Ullery, Jr. | 136/89 P |
| 4,296,148 | 10/1981 | Friese | 427/125 |
| 4,338,362 | 7/1982 | Turcotte | 427/314 |
| 4,490,411 | 12/1984 | Feder et al. | 427/463 |
| 4,773,376 | 9/1988 | Uchikawa et al. | 123/489 |
| 5,032,568 | 7/1991 | Lau et al. | 505/1 |
| 5,169,513 | 12/1992 | Mase et al. | 204/429 |
| 5,372,775 | 12/1994 | Hayashi et al. | 419/10 |

*Primary Examiner*—Shrive Beck
*Assistant Examiner*—Michael Barr
*Attorney, Agent, or Firm*—Venable; George Spencer; Norman N. Kunitz

[57] ABSTRACT

A process for applying materials to a carrier, for which the material is atomized just prior to applying it by compressed air that is supplied separately. The process is particularly suited for the application of electrically conductive material to carriers of ceramics materials.

16 Claims, 3 Drawing Sheets

PROCESS OF APPLYING MATERIAL, IN PARTICULAR FOR THE PRODUCTION OF ELECTRODES FOR EXHAUST GAS SENSORS

CROSS-REFERENCE TO RELATED APPLICATION

This application claims the priority of Patent Application Serial No. 1 96 14 147.8 filed in Germany on Apr. 10, 1996, the subject matter of which is incorporated herein by reference.

BACKGROUND OF THE INVENTION

The invention is based on a process of applying material with a defined structure to a carrier.

Processes for producing electrically conductive regions, such as conductive surface patterns, conductor tracks, printed circuits and the like are known. Surface patterns are applied, for example, by rolling them on or spreading them on. For planar probes, the electrodes and conductor tracks are generally applied to ceramic substrates with the screen printing technique, wherein the electrode or conductor track material can, for example, be applied as Cermet paste and subsequently sintered. Furthermore, a technique for applying an exhaust gas/oxygen/sensor electrode (Lambda probe) is known from German Laid-Open Patent Application No. DE-OS 30 14 877, for which an electrically conductive liquid or paste is injected into a hollow element by metering it and is distributed inside the hollow element by means of a finger-shaped, inflatable part. German Published Patent Application No. DE-AS 17 71 551 describes a process for printing electrical circuits onto a substrate where a conductive paste is applied to a substrate through a translatory movement of an elastic transfer device. Finally, German Published Patent Application No. DE-A1 32 25 483 describes a process for producing electrically conductive regions, wherein an electrically conductive paste is applied pointedly to predetermined regions of a preferably uneven carrier by means of an elastically deformable stamp in a printing process, and wherein the stamp is designed as printing roller as well as performs a rotational movement for applying continuous or endless patterns.

The described processes are in part very involved with respect to production technology. In addition, the known processes permit only a rather unspecific application of the electrically conductive material, so that this material frequently is also applied to places where it is technically not required. However, especially when using expensive, electrically conductive materials, it is desirable to apply those only where they are absolutely needed.

SUMMARY OF THE INVENTION

The basic process according to the invention involves a process for applying material with defined structures onto a ceramic carrier, wherein the material is sprayed onto the carrier. In contrast, to the known processors described above, the according to the invention has the advantage that it is possible to reduce the amount of material used as a result of a specific application of materials to the regions where they are technically required.

More particularly, the invention involves a process for applying material with defined structures to a carrier, wherein the material is sprayed onto the carrier and the air used for the spraying as well as the material are supplied separately and are subsequently atomized. The inventive process thus provides for a separate feeding of the air for spraying and the material, e.g. via two separate tubes. These tubes and in particular their discharge openings preferably are arranged at a pointed angle or at a right angle to each other, wherein their free end openings meet. In the region where the end openings for the two feed tubes meet, the supplied material is atomized by the air for spraying. Thus, the atomizing and application location for the material is locally limited and permits a specific application of the material to the carrier. Accordingly, the material is applied only to the technically required locations on the carrier and thus permits a considerable savings in the frequently costly, e.g. electrically conductive materials. Also, the atomizing of the material outside of the tubes avoids problems during the material feeding, which can consist in the wear or the blocking of the tubes. The specific way of applying the materials also makes it possible to apply precise contours, such as conductive surface patterns, conductor tracks, insulating layers or strips, printed circuits and the like, wherein it is advantageous that maskings such as those needed for the screen printing or for the etching techniques can be omitted. In addition, a coating can be applied advantageously to the inside of bores and hollow spaces to produce, for example, internal electrodes.

For another embodiment, the invention concerns the aforementioned process, wherein the air is supplied under pressure via a first tube. The air pressure provided according to the invention permits a complete and fine atomization of the material and, as a result of the close coordination of the inventive discharge openings for the air feed tube and the material feed tube has a suction effect onto the latter. An air pressure of >0.01 bar, in particular 0.01 bar to 7 bar has proven to be particularly advantageous. Another embodiment according to the invention provides that the material is fed through a second tube under comparably low pressure.

According to a modification of the invention, an above-described process is made available, for which the feeding of the air and/or the material is metered. The metering of the supplied air and especially the supplied material permits an application of the material that meets the most varied technical requirements, wherein this also saves costs.

In accordance with one modification of the invention, sintered-on or sintered ceramic materials are provided as the carrier.

The invention furthermore provides advantageously that the described process be carried out with materials in the form of pastes or suspensions. The process is especially preferred for use with materials, e.g., ceramic materials, which have to undergo a drying process, are baked on, sintered or sintered-on after they have been sprayed on and thus can live up to their function. In particular electrically conductive materials are used in an especially advantageous way, which materials contain cermet, perovskite or precious metals such as, for example, metals of the platinum group, in particular platinum, palladium or rhodium, or are composed of these. Of course, the inventive process is suitable for any other type of material as well, which can be applied with defined structures such as surface patterns, conductor tracks or printed circuits. A combination of different substances such as platinum and zirconium dioxide can also be used according to the invention. In accordance with the invention, the materials can also contain ceramic and/or glass powder preparations as well as organic admixtures. Finally, in particular insulating materials can also be used according to the invention in addition to the aforementioned electrically conductive materials, so that insulating layers can, for example, be sprayed onto ceramic carriers.

In accordance with the invention, the described processes are used especially and preferred for applying electrodes, preferably internal electrodes or conductor tracks to carriers. The invention is particularly suited for applying electrodes to exhaust-gas sensors, in particular for applying internal electrodes to Lambda probes. However, the invention is also suited for applying terminal conductor tracks to Lambda probes. Finally, the inventive process can also be used for applying resistance or insulating pastes.

The invention additionally concerns a device for carrying out the inventive process. The device is distinguished by two tubes for supplying air or gases (e.g. nitrogen, nitrogen mixtures) and, for example, electrically conductive material, for which the discharge opening are arranged at a pointed or right angle to each other. The supplied material is atomized and applied to the carrier in the region where the two discharge openings are arranged.

Depending on the angle and arrangement of the discharge openings for the tubes, the material is sprayed in an axial or side direction, relative to the longitudinal axis of the material feed tubes. In any case, with respect to the angle and distance to each other, the discharge openings must be arranged such that the exiting air permits a spraying of the supplied material onto the substrate. With the preferred parallel arrangement of the end regions for the two tubes and the preferred end-side location for the discharge opening of the material feed tube, as well as an equally preferred side-discharge opening for the air feed tube that projects beyond the material feed tube, the material is sprayed between the discharge openings to the side, in accordance with the right angle that is formed, thus permitting an easy application of internal electrodes in hollow spaces or bores. The air supply tube is preferably connected to a compressed air generator, while the feed tube for the material to be applied leads to storage container.

These and other features and advantages of the invention will be further understood from the detailed description below of the preferred embodiments with reference to the accompanying drawings.

DETAILED DESCRIPTION OF THE PREFERRED EMBODIMENTS

Figure 1:
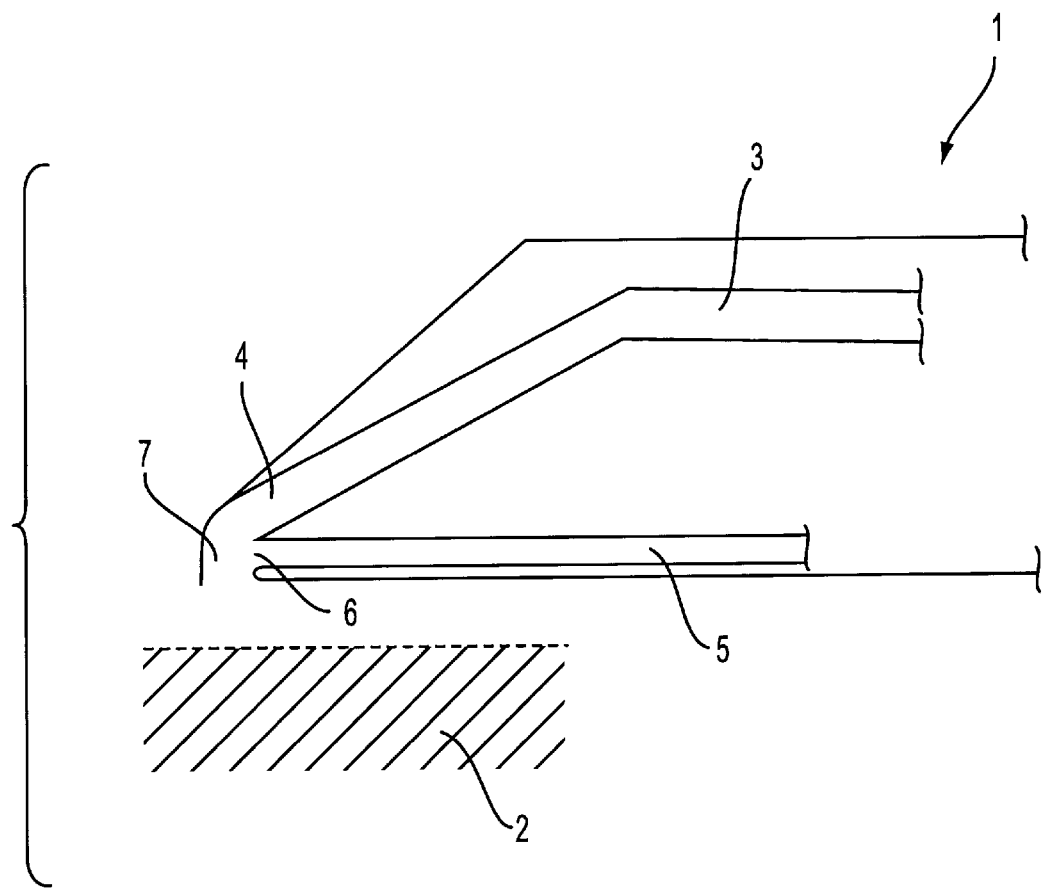
FIG. 1 is a schematic longitudinal sectional view of a device according to the invention.

FIG. 1 shows a device 1 for carrying out the inventive process, that is for applying material to a carrier 2. The inventive device is distinguished by an air feed tube 3 with a discharge opening 4. In accordance with the invention, the device also has a feed tube 5 for materials with a discharge opening 6. The discharge openings 4 and 6 meet at a sharp or acute angle and form an atomizing space 7. The air supply line 3 is preferably connected to a compressed air blower that is not shown here. The material feed tube 5 is preferably connected to a storage container for this material, which is not shown here.

In accordance with the inventive process, compressed air flows through the tube 3 and through discharge opening 4 into the atomizing space 7. Material, e.g. in the form of a paste or a suspension, flows with a lower pressure through the second, material-feed tube 5, then through the discharge opening 6 and into the atomizing space 7. As a result of the strong air flows present there, the material is atomized and flows through the opening of the atomizing space directly and pointedly onto the carrier 2. It is preferable if the air supply as well as the material supply is metered, thus permitting a precise arrangement of electrodes or conductor tracks on the carrier 2, e.g., a ceramic.

It is of course possible according to the invention to have different arrangements of the two tubes to each other and the discharge openings for the atomizing space and the tubes. Among other things, the separate feeding of the air, preferably with high pressure, and the feeding of the electrically conductive material with, for example, low pressure, is important according to the invention, wherein the electrically conductive material is atomized only outside of the feed tubes. Thus, the invention can also provide that a spatially defined atomizing space is omitted. In such a case, which is shown in FIGS. 2 to 5, the discharge openings for the two tubes meet while no spatially defined atomizing space is created.

Figure 2:
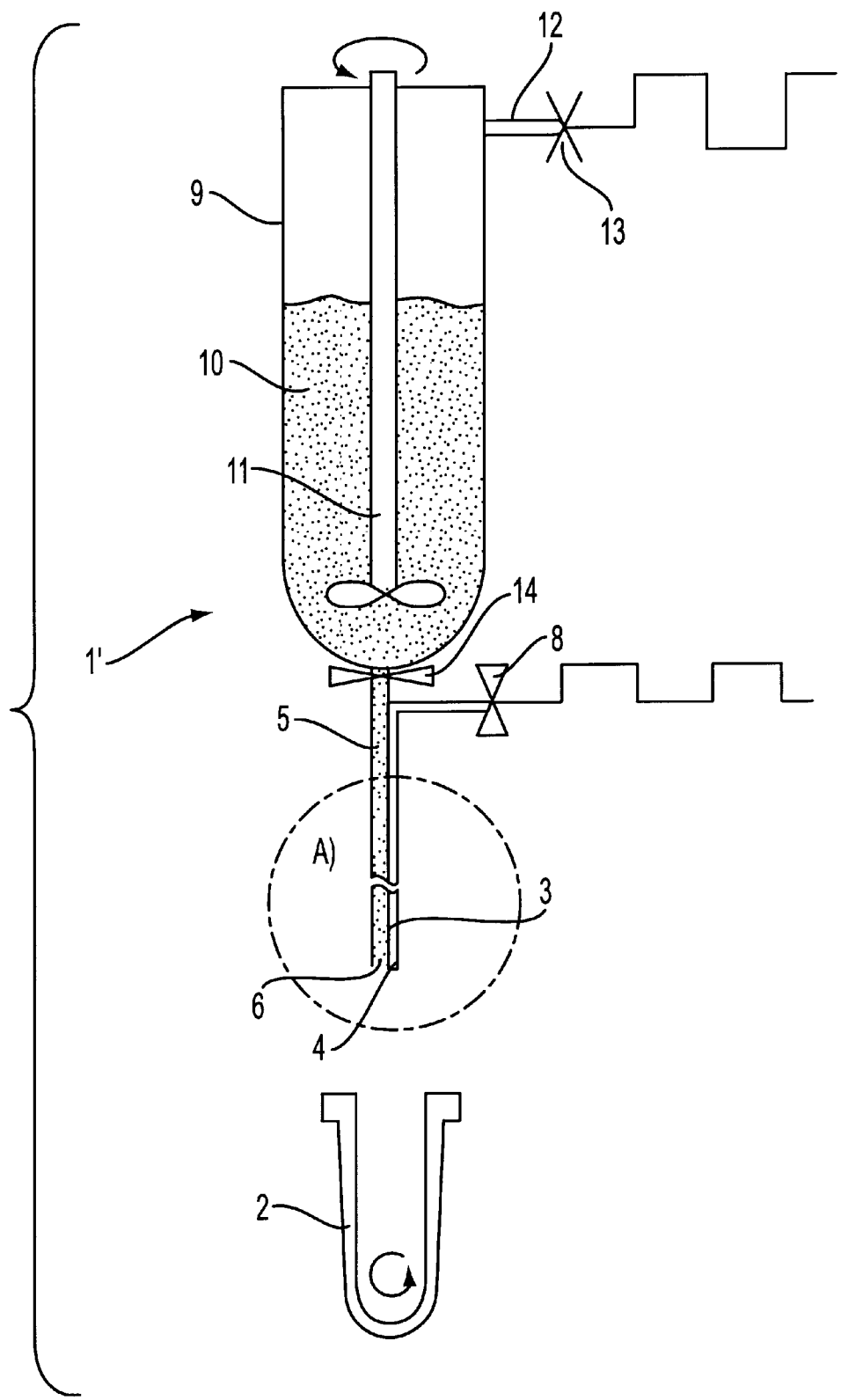
FIG. 2 is a schematic longitudinal sectional view of another embodiment of a device according to the invention, including the storage container.

FIG. 2 shows another embodiment 1' of the inventive device for applying material 10 onto a substrate 2. The inventive device 1' comprises a storage container 9 that holds the material 10 and which can accommodate, for example, 0.1 to 10 liters of material, as well as a twirling stick 11 disposed inside of the storage container 9. In the upper region, the storage container 9, a pressure compensating line 12 with a valve 13 opens in the container 9. A material feed tube 5 is coordinated with or connected to the storage container 9, with a valve 14 being located between the storage container 9 and the tube 5. Coordinated with and parallel to the outlet end region for the feed tube 5 and directly adjacent to it, is the outlet end region for the air feed tube 3, which has a valve 8 in the region that does not adjoin the tube 5. At its outlet end, the air feed tube 3 projects or extends beyond the end of the material feed tube 5. Tube 5 has a discharge opening 6 at its outlet end while tube 3 has its discharge opening 4 on the side of the tube 3 facing and adjacent the discharge tube opening 6.

Figure 3:
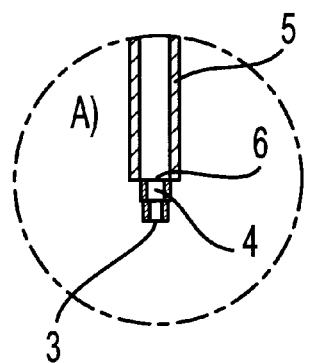
FIGS. 3, 4 and 5 are schematic detail views of a portion A of the device according to the embodiment of the invention shown in FIG. 2.
Figure 4:
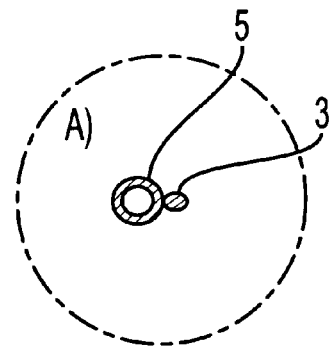
Figure 5:
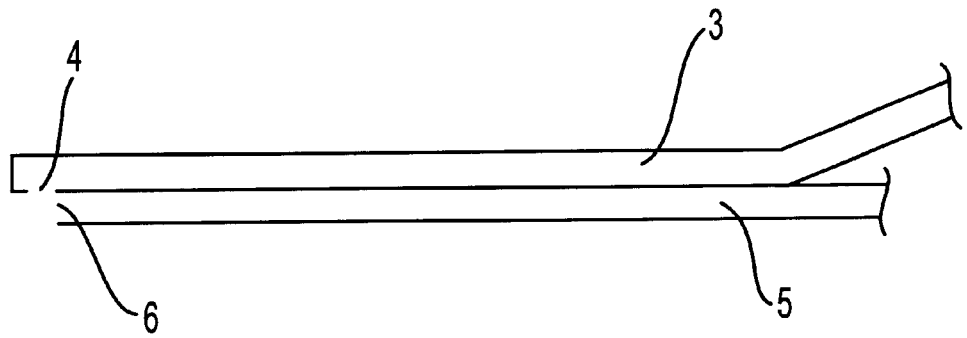

FIGS. 3, 4 and 5 show detailed views of the region A of the inventive device according to FIG. 2, in particular the end regions of the air and material feed tubes, that is the spray head. It follows from FIG. 3 that the end of air supply tube 3 with its discharge opening 4 projects or extends beyond the and of the material supply tube 5 with its discharge opening 6. The two discharge openings 4 and 6 are therefore at a right angle to each other as clearly can be seen in FIG. 5. The axial distance between discharge opening 4 of tube 3 and the discharge opening 6 of tube 5 preferably lies between 0.5 mm to 2 mm. The inside diameter of tube 5 can be between 0.2 mm and 2.5 mm. Depending on the area to be sprayed, the inside diameter of the discharge opening 4 of tube 3 can be >0.2 mm. The inside diameter of the tube 3 is >0.5 mm. FIG. 4 is a view from above of the two tubes 3 and 5. The view from above shows the open ending of tube 5 with discharge opening 6 as well as the closed ending of tube 3. FIG. 5 shows a longitudinal cut of the end region (spray head) of the inventive device, which also reveals the parallel, adjoining arrangement of the two tubes in their respective discharge end regions as well as the arrangement of openings 4 and 6 at a right angle to each other. The end regions for tubes 3 and 5 that run parallel to each other can be one to five hundred millimeters long, depending on the spray element.

The material 10 to be applied is placed into the storage container 9. In the storage container 9, the material, e.g., in the form of a suspension or paste, is stirred with a fan-type stirrer 11 at 50 to 3000 rotations/minute. The storage container 9 is attached to a three-axis CNC controlled positioning unit. A pressure of 0.07 to 0.80 bar can be adjusted via the pressure balancing line 12 and the valve 13.

The carrier to be processed, meaning the element to be sprayed, for example, a sensor ceramic carrier, is inserted into a rotatable holder that is also CNC controlled and permits rotation around the longitudinal axis of the ceramic carrier 2. FIG. 2 shows the inside bore of a sensor ceramic carrier 2. With CNC control, the tubes 3 and 5 are driven or moved vertically into the inside bore of the carrier 2. The valves 8 and 14 for the air and material feed tubes 3 and 5 are opened as soon as the discharge openings 4 and 6 of the tubes are inside the inside bore of the carrier 2. The air flows out of the opening 4 with a pressure of 0.01 to 7 bar. The material 10 to be applied flows out of the discharge opening 6 of tube 5 and is sprayed to the side, i.e., literally, owing to the air flow that affects the discharging material 10. The conductive lead line is applied to the inner surface of the carrier while the tubes are inserted into the inside bore of the ceramic carrier. The CNC control subsequently turns the ceramic 2 once around the longitudinal axis, thereby creating a ring of applied material. The tubes 3 and 5 are then pulled back by a defined distance and the ceramic carrier 2 is rotated another time around the longitudinal axis. A ring of applied material is again created on the inner surface of the carrier 2 in the inside bore. The spraying time for each spraying surface can be between 0.001 and 99 s. The valves for the air and material feed are then closed, and the tubes 3 and 5 are pulled out of the bore of the ceramic carrier.

The inventive device permits a precise application of the desired material in any optional contour, even on surfaces that are traditionally hard to process.

Exemplary Embodiment 1

The application of an inside electrode of a sensor ceramics for gas sensors I.

A cermet suspension containing precious metals, such as described in DE 4100107, is filled into a storage container with plastic liner. The suspension is stirred inside the storage container with a wing-type stirrer at approximately 500 RPM. The storage container with spray head (tubes) is attached to a three-axis CNC controlled positioning unit (compare FIG. 2).

In order to apply the inside electrode to the carrier, the presintered sensor element or carrier is fastened in a rotatable holder that is also CNC controlled and permits a rotation around the longitudinal axis of the ceramic carrier. The feed tubes 3 and 5 are inserted vertically into the inside bore of the ceramic carrier. The valves for the air and material feed are opened as soon as the discharge openings of the tubes enter the bore of the carrier. The material is squeezed out of the tube (inside diameter=1.2 mm) with a pressure of approximately 0.2 bar. The air has a pressure of 1 bar (tube: inside diameter=0.9 mm; closed at the end, with side discharge opening of 0.3 mm inside diameter). Accordingly, the material is sprayed to the side, i.e., laterally relative to the longitudinal axis of the bore. The spraying head formed by tubes 3 and 5 is inserted approximately 30 mm into the inside (interior) bore of the ceramic carrier where the lead line is to be applied to the carriers inner surface. The ceramic carrier 2 is then rotated within 1 second around the longitudinal axis by 360°. Subsequently, the spraying head is pulled back by about 1 mm and the ceramic carrier is rotated a second time by 360°. Two rings of cermet are formed in this way in the inside bore of the ceramic carrier, which rings form the inside electrode. Following this, the respective valves for the air and material supplies are closed, and the tubes of the spraying head pulled out of the ceramic carrier. The ceramic carrier is then dried and subsequently sintered.

Exemplary Embodiment 2

Application of an inside electrode for a sensor ceramic carrier for gas sensors II.

Creating the suspension containing precious metals (electrode paste):

Composition:
    40% in weight platinum powder
    5% in weight $\alpha$-$Al_2O_3$ powder in 25% in weight terpineol
    24% in weight ethanol
    3% in weight alkyl cellulose and
    3% in weight additive.

The mixture is then homogenized for 2 h in a suitable device(e.g., planetary mill).

The suspension with precious metals is placed into a storage container 9 with a plastic liner. Inside the storage container, the suspension is stirred at approximately 500 RPM with a wing-type stirrer. The storage container with spray head (tubes) is fastened to a three-axis CNC controlled positioning unit (see FIG. 2).

The outside electrode is then applied and the ceramics subsequently sintered.

In order to apply the inside electrode, the sensor element, which is also CNC-controlled and can rotate, is inserted into a holder that permits a rotation around a longitudinal axis of the ceramic carrier. The material and air tubes are inserted vertically into the inside bore of the ceramic carrier or sensor element. The valves for the air and material supply are opened as soon as the discharge opening for the tubes enter the inside bore. The material is squeezed out of the tube (inside diameter=0.8 mm) with a pressure of approximately 0.5 bar. The air has a pressure of 2.5 bar (tube: inside diameter 0.6 mm; closed at the end, with a side discharge opening of 0.2 mm inside diameter). Accordingly, the material is sprayed to the side. The tube is inserted approximately 20 mm into the inside bore of the ceramic carrier, where the conductive lead line is to be applied. The ceramic carrier is then turned or rotated around the longitudinal axis by 360° within one second. Subsequently, the tube is pulled back approximately 0.8 mm and the ceramic carrier is turned or rotated a second time by 360°. Two rings of electrode paste are produced in this manner or the inner carrier surface within the inside bore of the ceramic carrier. Following this, the valves for the air and material supplies are closed and the tubes pulled out of the bore of the ceramic carrier. The ceramic carrier is dried, and the inside electrode is subsequently baked in a reducing atmosphere (5% $H_2$ in $N_2$).

According to the invention, it is also possible to provide for a feeding of the material or air through more than one tube respectively. In such a case, a device for carrying out the inventive process has a corresponding multiple number of feed tubes, for example three or four.

It will be understood that the above description of the present invention is susceptible to various modifications, changes and adaptations, and the same are intended to be comprehended within the meaning and range of equivalents of the appended claims.

What is claimed is:

1. A process of applying an electrode to a carrier of ceramic material, said process comprising the steps of:
    providing a tube-shaped carrier of ceramic material;

supplying electrode material to a spray tube which produces a laterally directed spray of the electrode material;

advancing the spray tube into the hollow space of the tube-shaped carrier along a longitudinal axis of the tube-shaped ceramic carrier while non-rotating and while spraying the electrode material to apply a lead-in conductive track of the electrode material on the inner side wall of the tube-shaped ceramic carrier; and subsequently, rotating the tube-shaped ceramic carrier about its longitudinal axis relative to the spray-tube while continuing the spraying to produce a first ring-shaped electrode on the inner side wall of the tube-shaped ceramic carrier and in contact with the conductive track.

2. A process according to claim 1, wherein the step of spraying includes separably supplying the electrode material and air used for the spraying to the spray tube, and subsequently atomizing the electrode material with the air.

3. A process according to claim 2, wherein the air is supplied through a first tube under a pressure greater than >0.01 bar.

4. A process according to claim 3, wherein the electrode material is supplied through a second tube under lower pressure.

5. A process according to claim 4, wherein the step of atomizing includes disposing discharge openings for the tubes at an acute angle or at a right angle to each other.

6. A process according to claim 2, wherein a metered feeding of at least one of the air and the electrode material takes place.

7. A process according to claim 1, wherein the carrier is composed of one of sintered-on or sintered ceramic material or is coated with sintered ceramic material.

8. A process according to claim 1, wherein the material is supplied in the form of a paste or suspension.

9. A process according to claim 1, wherein the electrode material is electrically conductive.

10. A process according to claim 9, wherein the electrode material is cermet.

11. A process according to claim 1, wherein the electrode material contains or is composed of perovskite, or a precious metal, from the group of platinum, palladium and rhodium.

12. A process according to claim 1, wherein the electrode is applied to a carrier of an exhaust-gas sensor. subsequently, rotating the tube-shaped ceramic carrier about its rotational axis, relative to the spray-tube while continuing the spraying to produce a ring-shaped electrode on the inner side wall of the tube-shaped ceramic carrier.

13. A process according to claim 1, wherein the step of rotating comprises rotating the tube-shaped carrier once by 360°.

14. A process according to claim 1, wherein the tube-shaped carrier is vertically oriented, and said step of advancing includes advancing the spray tube vertically into the hollow space of the tube-shaped carrier.

15. A process of applying an electrode to a carrier of ceramic material, said process comprising the steps of:

providing a tube-shaped carrier of ceramic material;

supplying electrode material to a spray tube which produces a laterally directed spray of the electrode material;

advancing the spray tube into the hollow space of the tube-shaped carrier along a longitudinal axis of the tube-shaped ceramic carrier while non-rotating and while spraying the electrode material to apply a lead-in conductive track of the electrode material on the inner side wall of the tube-shaped ceramic carrier;

subsequently, rotating the tube-shaped ceramic carrier about its longitudinal axis relative to the spray-tube while continuing the spraying to produce a first ring-shaped electrode on the inner side wall of the tube-shaped ceramic carrier; and, following the step of rotating, stopping the rotation and linearly withdrawing the spray tube for a given distance and then again rotating the tube-shaped ceramic carrier about its rotation axis relative to the spray-tube to form a second ring-shaped electrode, that is linearly spaced from the first ring shaped electrode, on the inner side wall of the tube shaped ceramic carrier; and thereafter discontinuing the spraying and withdrawing the spray tube from the hollow interior space of the tube-shaped ceramic carrier.

16. A process according to claim 15, wherein the steps of rotating, in each case, comprise rotating the tube-shaped carrier once by 360°.

* * * * *